US006788407B1

United States Patent
Higdon et al.

(10) Patent No.: US 6,788,407 B1
(45) Date of Patent: Sep. 7, 2004

(54) LASER INTERROGATION OF SURFACE AGENTS

(75) Inventors: Noah Scott Higdon, Sandia Park, NM (US); Dale Allen Richter, Sandia Park, NM (US); Patrick Louis Ponsardin, Placitas, NM (US); Thomas Herman Chyba, Tijeras, NM (US); Wayne Thomas Armstrong, Albuquerque, NM (US); Clarence Theodore Lobb, III, Albuquerque, NM (US); Brian Thomas Kelly, Albuquerque, NM (US); David Michael Sanchez, Albuquerque, NM (US); Robert D. Babnick, Albuquerque, NM (US); Quang Duy Bui, Albuquerque, NM (US); Waverly Dickson Marsh, Albuquerque, NM (US)

(73) Assignee: ITT Manufacturing Enterprises, Inc., Wilmington, DE (US)

( * ) Notice: Subject to any disclaimer, the term of this patent is extended or adjusted under 35 U.S.C. 154(b) by 0 days.

(21) Appl. No.: 10/098,627

(22) Filed: Mar. 18, 2002

(51) Int. Cl.[7] .................. G01N 21/65; G01N 21/64; G01J 3/44
(52) U.S. Cl. .................. 356/301; 356/318; 356/328
(58) Field of Search .................. 356/301, 326, 356/328, 318

(56) References Cited

U.S. PATENT DOCUMENTS

| 4,247,770 A | * | 1/1981 | Welch .................. 356/301 |
| 4,373,782 A | | 2/1983 | Thelen |
| 4,489,239 A | * | 12/1984 | Grant et al. .......... 250/339.03 |
| 4,959,840 A | | 9/1990 | Akins et al. |
| 5,191,525 A | | 3/1993 | LeBrun et al. |
| 5,257,085 A | | 10/1993 | Ulich et al. |
| 5,305,082 A | * | 4/1994 | Bret .................. 356/328 |
| 5,420,723 A | * | 5/1995 | Galle .................. 356/303 |
| 5,450,125 A | | 9/1995 | Ulich et al. |
| 5,491,344 A | | 2/1996 | Kenny et al. |
| 5,521,703 A | * | 5/1996 | Mitchell .................. 356/301 |
| 5,638,173 A | | 6/1997 | Smith et al. |
| 5,689,333 A | | 11/1997 | Batchelder et al. |
| 5,850,623 A | | 12/1998 | Carman, Jr. et al. |
| 5,982,795 A | | 11/1999 | Rothweil et al. |
| 6,608,677 B1 | | 8/2003 | Ray et al. |

FOREIGN PATENT DOCUMENTS

GB          2220741 A     1/1990

OTHER PUBLICATIONS

Ray, Mark D, et al., "Ultraviolet mini–Raman lidar for stand–off, in situ identification of chemical surface contaminants" Review of Scientific Instruments, vol. 71, No. 9, Sep. 2000, pp. 3485–3489.
Thermo Nicolet Lab Systems, "Nicolet FT–Raman Spectrosopy", The History of Raman Spectroscopy, 2001, 2 pp., www.nicolet.com/labsys/products/Raman_History.html.
McCarthy, Daniel C, "Alexandrite Laser is Attuned to Flexible Lidar System", Photonics Applications, Feb. 2001, 2 pp., www.photonics.com/spectra/applications/feb01/apps alexandrite.html.
Ray M.D. et al., "Ultraviolet Mini–Raman Lidar for Stand–off, in SITU Identification of Chemical Surface Contaminants" Review of Scientific Instruments, American Institute of Physics; New York, vol. 71, No. 9, Sep. 2000; pp. 3485–3489.

* cited by examiner

Primary Examiner—F. L. Evans

(57) ABSTRACT

An apparatus for laser interrogation of surface agents moving relative to the apparatus. A receiver telescope includes a secondary reflector that may compensate for variations in distance from a target to the laser. The secondary reflector relies on a distance to target signal that may be collected at a point substantially away from the target, in the direction of relative motion, to allow a focusing mechanism time to react.

64 Claims, 8 Drawing Sheets

SKETCH OF KEY
GEOMETRIC PARAMETERS

DEFINING THE TIME INTERVAL TLR

G) ADJUST FOCUS OF RECEIVER TELESCOPE

GA) RECEIVE RANGE-TO-TARGET DATA SAMPLE

GB) TAG RANGE-TO-TARGET DATA SAMPLE WITH TIME SEQUENCE

GC) RECEIVE RELATIVE MOTION DATA SAMPLE

GD) CALCULATE RATE OF CHANGE OF RELATIVE MOTION

GE) CORRECT RANGE-TO-TARGET DATA SAMPLE FOR RELATIVE MOTION

GF) CORRECT RANGE-TO-TARGET DATA SAMPLE FOR RATE OF CHANGE OF RELATIVE MOTION

GG) CORRECT RANGE-TO-TARGET DATA SAMPLE FOR LASER PULSE RATE

GH) CORRECT RANG-TO-TARGET DATA SAMPLE FOR RANGE-FINDER PULSE RATE

GI) CORRECT RANGE-TO-TARGET DATA SAMPLE FOR RANGE-FINDER POSITION RELATIVE TO RECEIVER TELESCOPE LINE-OF-SIGHT

GJ) CORRECT TAGGED RANGE-TO-TARGET DATA SAMPLE FOR LASER AND RANGEFINDER WAVEFORM DE-SYNCHRONIZATION TIME OFFSET

GK) TRANSFORM SET OF CO-ORDINATES OF CORRECTED TAGGED RANGE-FINDER SAMPLE TO RECEIVER TELESCOPE LINE-OF-SIGHT

GL) CONVERT RANGE-TO-TARGET SAMPLE TO EQUIVALENT RECEIVER TELESCOPE SECONDARY REFLECTOR POSITION

FIG.12

LASER INTERROGATION OF SURFACE AGENTS

BACKGROUND OF THE INVENTION

1. Field of the Invention

The present invention relates generally to determination of the identity of surface agents such as surface-deposited chemicals.

2. Description of the Background Art

The identification of chemical agents may be conducted under adverse conditions. Such identification may be carried out, e.g. in the field, or at a material entry point. Chemical agents to be identified, may be e.g. hazardous or toxic. Personnel engaged in such identification may wish to be protected from the chemicals by an enclosure. In this way equipment used to perform the identification may be exposed to the substance, while the personnel who operate the equipment are not.

Raman spectroscopy is one means of identifying unknown chemical agents. Raman spectroscopy equipment, however, is typically designed for static placement in laboratories, and may therefore lack ruggedness and mobility. Raman spectroscopy equipment may not be adapted to relative motion between the equipment and an unknown chemical agent. Such equipment may be large and heavy, and the individual components may not be integrated to the degree required for use in the field.

Raman spectroscopy equipment may be placed next to, e.g. a conveyor system carrying objects of various shapes or sizes, on a vehicle, or next to a gate through which objects, such as, e.g. vehicles may be traveling. In cases such as these there may be relative motion between the Raman spectroscopy equipment and the chemical agent to be analyzed.

Ray et al., "Ultraviolet mini-Raman LIDAR for Stand-off, in situ Identification of Chemical Surface Contaminants", e.g. describes a related device using the Raman effect. The device is described as portable and rugged enough to be transported in a standard minivan, and capable of operating within minutes of arriving at a scene.

Raman spectroscopy equipment used in a laboratory may have a relatively long time window in which to view a sample. A laboratory sample may be analyzed several times to determine of its identity. Raman spectroscopy equipment that is placed next to a conveyor or on a vehicle, on the other hand, may have only a limited period of time in which to analyze a chemical agent. It would thus be desirable for mobile Raman spectroscopy equipment to be able to analyze a chemical agent in a relatively brief period of time, as e.g. a vehicle traverses the ground or a package moves along a conveyor system. It would also be desirable for the identity of a chemical agent to be determinable in a limited number of pulses of, e.g. an output beam.

Raman spectroscopy equipment that is mounted on an operational vehicle or alongside a conveyor system may be, e.g. located within in short distance, such as, e.g. two meters, of a chemical agent. It would thus be desirable for Raman spectroscopy equipment to be capable of efficient light collection at that range. Moreover, a distance between the Raman spectroscopy equipment and a chemical agent may vary significantly over time due to, e.g. rugged terrain or a random placement of packages on a conveyor. It would thus be desirable for an optical system to be capable of adjusting its focus to compensate for distance variation.

In the event Raman spectroscopy equipment may be used, e.g. in military applications, the equipment may be required to operate for extended periods of time without extensive maintenance. It would be desirable, therefore, for the equipment to be able to function reliably for extended periods of time.

Raman spectroscopy equipment may become contaminated by the chemical agents which it analyzes. Raman spectroscopy equipment is normally decontaminated by, e.g. washing it with a chemical, such as, e.g. a chemical solvent. The decontamination process may, however, harm sensitive components comprising the Raman spectroscopy equipment. It would be desirable for Raman spectroscopy equipment to be resistant to contamination from the chemical agents to be analyzed. It would further be desirable for Raman spectroscopy equipment that will be decontaminated to be resistant to chemicals used during the decontamination process. It would further be desirable for Raman spectroscopy equipment that is mounted outside a vehicle or an enclosure to offer no contamination path into the vehicle or enclosure.

In the event that Raman spectroscopy equipment uses an Excimer laser, the gas inside the Excimer laser may have to be replaced periodically. It would be desirable, therefore, for such a replacement to be relatively quick and easy to perform, so the operation of the equipment is interrupted minimally.

Fluorescence of, for example, the surroundings of a chemical agent may interfere with determining an identity of the chemical agent. Soils, in particular, exhibit significant fluorescence when subjected to laser light. It would be desirable, therefore, for the effect of such fluorescence on the analysis of chemical agents to be minimized.

Raman spectroscopy equipment may well be unable to identify a particular chemical agent. The inability to identify the chemical agent may be due to, e.g. the chemical agent having not been encountered previously, or a malfunction of the equipment. It would be desirable for Raman spectroscopy equipment that comes upon a new or unidentifiable substance to be able to store a signature of the chemical agent for later analysis or troubleshooting. In the meantime, it would be desirable for a list of known chemical agents to be updated to include the new or unidentifiable chemical agent so that a frequency of occurrence of the chemical agent can be determined.

There remains a need in the art, therefore, for a transportable Raman spectroscopy device that is capable of analyzing chemical agents moving relative to the device, in the presence of soil fluorescence, without being compromised unduly by decontamination procedures.

SUMMARY OF THE INVENTION

The invention provides a relatively compact, lightweight, piece of Raman spectroscopy equipment.

In particular, in one aspect the invention provides an apparatus for laser interrogation of surface agents moving relative to the apparatus. A receiver telescope includes a secondary reflector that may compensate for variations in distance from a target to the laser. The secondary reflector relies on a distance to target signal that may be collected at a point substantially away from the target, in the direction of relative motion, to allow a focusing mechanism time to react.

In a second aspect the invention provides an apparatus for laser interrogation of surface agents moving relative to the apparatus. A receiver telescope includes a secondary reflector that may compensate for variations in distance from a target to the laser. The secondary reflector relies on a distance to target signal that may be collected at a point substantially away from the target, in the direction of relative motion, to allow a focusing mechanism time to react. The laser may emit pulses at a predetermined pulse rate, a variable pulse rate, an operator-controlled pulse rate, or a pulse rate that is proportional to a rate of relative motion of a target relative to the apparatus or a ground rate of relative motion of a vehicle.

In a third aspect the invention provides a system for laser interrogation of surface agents moving relative to the apparatus. A receiver telescope includes a secondary reflector that may compensate for variations in distance from a target to the laser. The secondary reflector relies on a distance to target signal output by a range finding means that may be collected at a point substantially away from the target, in the direction of relative motion, to allow a focusing mechanism time to react. The focusing means focuses the secondary reflector based on the distance-to-target signal and the rate of relative motion. A spectrograph receives the inelastically scattered radiation from the receiver telescope.

In a fourth aspect the invention provides a method for laser interrogation of surface agents moving relative to an interrogator in which a receiver telescope compensates for variations in distance from a target to the laser. The secondary reflector relies on a distance to target signal that may be collected at a point substantially away from the target, in the direction of relative motion, to allow a focusing mechanism time to react.

A spectrograph receives the inelastically scattered radiation from the receiver telescope, comparing the image of the dispersed spectrum of the target substance to an image of a spectrum of inelastically scattered radiation of a known substance, identifying the target substance if the image of the dispersed spectrum of the target substance matches substantially the image of the inelastically scattered radiation of the known substance, and adding the target substance to a list of unidentified substances if the image of the dispersed spectrum of the target substance does not substantially match any image in database.

In a fifth aspect the invention provides a system for laser interrogation of surface agents moving relative to the apparatus. A receiver telescope includes a secondary reflector that may compensate for variations in distance from a target to the laser. The secondary reflector relies on a distance to target signal output by a range finding means that may be collected at a point substantially away from the target, in the direction of relative motion, to allow a focusing mechanism time to react. The focusing means focuses the secondary reflector based on the distance-to-target signal and the rate of relative motion. An optical fiber couples inelastically scattered radiation from the secondary reflector to a spectrograph.

In a sixth aspect the invention provides a system for laser interrogation of surface agents moving relative to the apparatus. A receiver telescope includes a secondary reflector that may compensate for variations in distance from a target to the laser. The secondary reflector relies on a distance to target signal output by a range finding means that may be collected at a point substantially away from the target, in the direction of relative motion, to allow a focusing mechanism time to react. The focusing means focuses the secondary reflector based on the distance-to-target signal and the rate of relative motion. An aluminum honeycomb structure carries the components relatively rigidly with respect to one another.

The above and other features and advantages of the present invention will be further understood from the following description of the preferred embodiments thereof, taken in conjunction with the accompanying drawings.

BRIEF DESCRIPTION OF THE DRAWINGS

FIG. 12 shows a sixth embodiment of the method shown in FIG. 7.

DETAILED DESCRIPTION OF THE PREFERRED EMBODIMENTS

Figure 1:
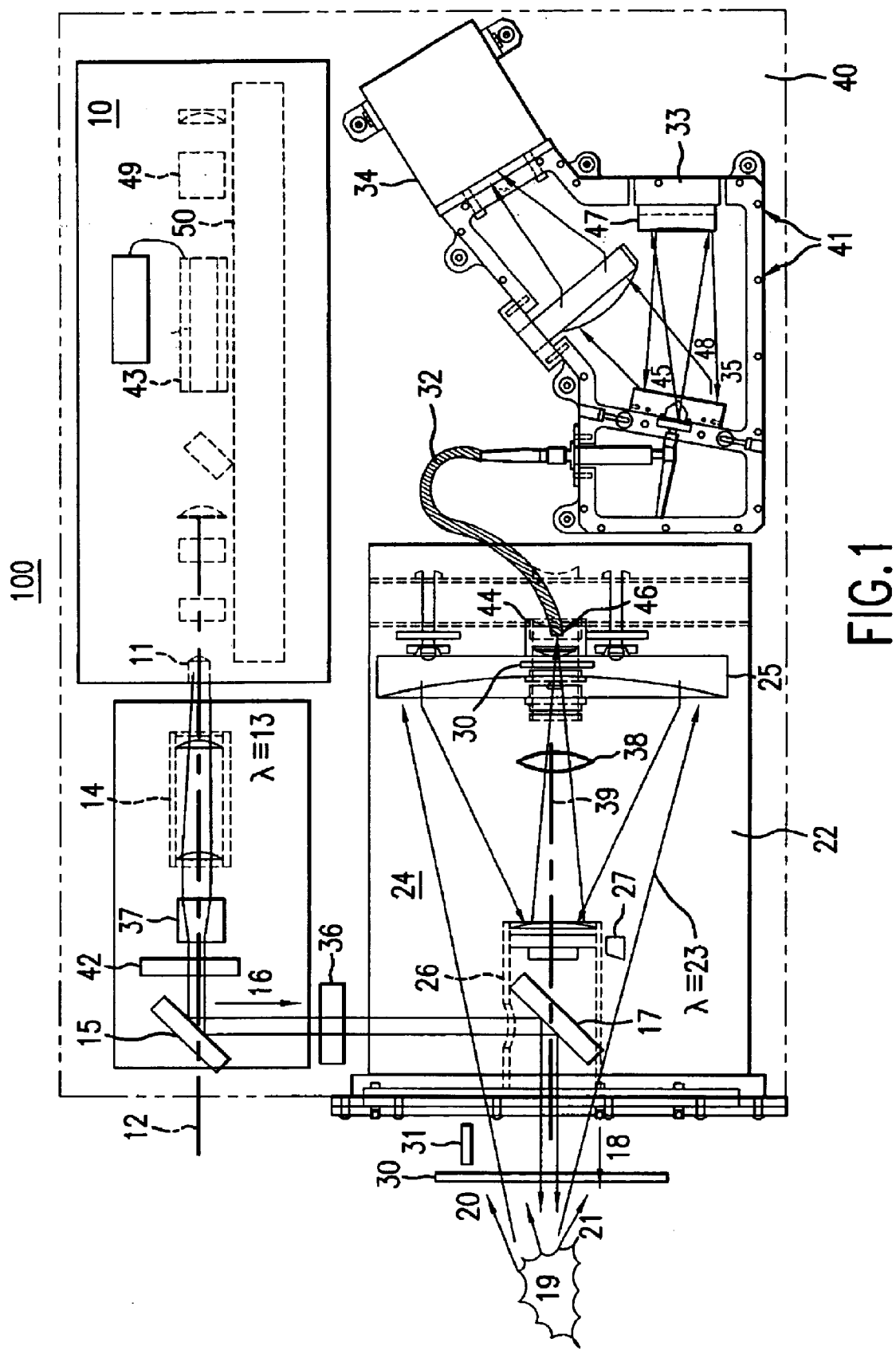
FIG. 1 is block diagram of an apparatus for laser interrogation of surface agents moving relative to the apparatus according to one embodiment of the invention.

In FIG. 1 is shown an apparatus 100 for laser interrogation of surface agents moving relative to the apparatus 100 according to one embodiment of the invention. FIG. 1 shows a laser 10 outputting an output beam 11, which has, e.g. an axis of transmission 12 and a predetermined wavelength 13. The laser 10 may produce an output beam 11 at a wavelength 13 which, e.g. minimizes soil fluorescence, such as, e.g. a wavelength 13 of less than about 253 nm, such as, e.g. approximately 248 nm.

Laser 10 may further include an optical component 49, which could be, e.g. a lens, a filter, or a reflector. In one embodiment, optical component 49 may be held in place with a retaining ring 50.

In one alternative embodiment, laser 10 is, e.g. an Excimer laser. If laser 10 is an Excimer laser, the output wavelength 13 of laser 10 may depend on a rare gas-halide with which the resonant cavity is filled. An Excimer laser with a resonant cavity filled with krypton-fluoride (KrF) gas may, e.g. output a wavelength of about 248 nm. Other rare gas-halides that may be used to fill a resonant cavity are, e.g. XeCl, KrCl, ArF, and XeF. In an alternative embodiment, laser 10 is, e.g. a line-narrowed Excimer laser.

Laser 10 may also comprise a replaceable gas bottle 43. If laser 10 were to include such a gas bottle 43, the rare gas-halide with Which the resonant cavity is filled could be replaced easily by changing out the gas bottle 43.

In another alternative embodiment, laser 10 may be, e.g. an Alexandrite laser, a tunable laser in which the resonant cavity is formed of a $BeAl_2O_4$ crystal into which $Cr^{+3}$ ions are embedded. If laser 10 were an Alexandrite laser, a wavelength 13 may be, e.g. converted to achieve a wavelength 13 of less than approximately 253 nm, for example 248 nm, as would be known to those skilled in the art. In another alternative embodiment, laser 10 may be, e.g. a line-narrowed Alexandrite laser.

In one embodiment, a beam 11 of laser 10 may be pulsed at a pulse repetition rate (PRR). In one alternative embodiment, the PRR may be made operator selectable. In a more preferred embodiment, the PRR may be variable. In another alternative embodiment, the PRR may depend upon a rate of motion of a target relative to the apparatus 100. A PRR that depends on a rate of relative motion of a target relative to the apparatus 100 may, e.g. allow a probability of detection of a surface agent to be optimized for the prevailing surface contamination distribution. characteristics by, e.g. matching the PRR to the rate of relative motion of the target relative to the apparatus 100.

The Raman spectroscopy system may, e.g. allow for rapid installation and removal of the sensor with minimal impact upon personnel time and vehicle integrity, since it may be self-contained. The Raman spectroscopy system may be, e.g. relatively small and lightweight in order to be easily installed and removed.

A beam-focusing telescope 14 may have an axis of transmission 12 and may focus substantially the output beam 11. A first reflector 15 also aligned with the axis of transmission 12 then directs the output beam 11 from the beam-focusing telescope 14 in a first direction 16, which may be substantially perpendicular to the axis of transmission 12.

An output axis 52 of laser 10 may be placed in various other orientations to the same effect by, e.g. adding reflectors, without deviating from the spirit of the invention. If output axis 52 is, e.g. rotated 90° relative to the position shown in FIGS. 1 and 2, a third reflector 53, as shown in FIG. 3, may be interposed between laser 10 and beam-focusing telescope 14 to re-direct the output beam 11 along axis of transmission 12. This might be the case if, e.g. the laser 10 performs or packages better in a particular orientation.

An output filter 36 may be, e.g. aligned with axis of transmission 12 or first direction 16, or both, to attenuate wavelengths other than wavelength 13.

In the alternative, a reflector coated to transmit predetermined wavelength 13 and reflect other wavelengths may be used, as would be known to those skilled in the art. In this manner undesired radiation, which may degrade the monochromaticity of the emitted output, such as that due to amplified spontaneous emission, can be reduced. An output polarizer 37 may also be, e.g. aligned with axis of transmission 12 or first direction 16, or both, to polarize output beam 11. Such a polarizer 37 may be followed by a filter 42 attenuating unpolarized radiation associated with the output beam, such as amplified spontaneous emission (ASE).

A second reflector 17 aligned with the first direction 16 then re-directs the output beam 11 in a second direction 18, which may be substantially perpendicular to the first direction 16. First reflector 15 and second reflector 17 may be placed in various other orientations to the same effect, by appropriately adjusting the orientations of first reflector 15 and second reflector 17, or by adding reflectors, without deviating from the spirit of the invention.

A target substance 19 substantially in line with the second direction 18 receives the redirected output beam 11, scattering at least some of it. The scattered radiation 20 includes elastically, or Rayleigh, scattered radiation 21 which may be at wavelength 13, and inelastically, or Raman, scattered radiation 22 which occurs at a spectrum of wavelengths 23 which are characteristic of the target substance 19.

A receiver telescope 24, preferably of the Cassegrain variety, having a focal direction 39 substantially opposite to said second direction 18 may be arranged to collect at least some of the inelastically scattered radiation 22. The receiver telescope 24 may be composed of a primary or receiver reflector 25 for collecting the inelastically scattered radiation 22, and a secondary or focusing reflector 26 for focusing the inelastically scattered radiation 22.

In one embodiment, primary reflector 25 may be disposed to reflect at least some radiation 22 scattered inelastically from target 19 toward secondary reflector 26. The surfaces of primary reflector 25 and secondary reflector 26 may be profiled to focus inelastically scattered radiation 22 at a first focal point 46, which may not be a focal point of either primary reflector 25 or secondary reflector 26 individually. First focal point 46 instead results from the combined effects of the surfaces of primary reflector 25 and secondary reflector 26 on the path of inelastically scattered radiation 22.

The location of first focal point 46 depends, in general, on the relative degrees of curvature of primary reflector 25 and secondary reflector 26. If, e.g. primary reflector 25 has a relatively greater degree of curvature than secondary reflector 26, rays of inelastically scattered radiation 22 that reflect from primary reflector 25 to secondary reflector 26 may converge substantially at first focal point 46.

Secondary reflector 26 may have a focusing mechanism 27, such as, e.g. a voice coil actuator, an electric motor, a piezoelectric actuator, a linear motor, a pneumatic actuator, or a hydraulic actuator to move secondary reflector 26 along focal direction 39 until inelastically scattered radiation 22 is focused at first focal point 46.

In one embodiment, either of the primary reflector 25 or secondary reflector 26 may be made to transmit substantially radiation of the polarization of the output beam 11, rather than reflecting it. In another embodiment, light of the polarization of the output beam 11 may be blocked by a lens 38 associated with, e.g. receiver telescope 24. Such a lens 38 may be, e.g. aligned substantially with said focal direction 39.

In one embodiment, any of the first reflector 15, second reflector 17, primary reflector 25, and/or secondary reflector 26 may be made to transmit substantially visible light, rather than reflecting it. Thus the visible component of sunlight may pass through the reflectors instead of being collected into receiver telescope 24.

In the preferred embodiment, the apparatus 100 may be designed to be resistant to a decontamination process, i.e.: the apparatus 100 may be subjected to high-pressure corrosive liquid chemical cleaning without adversely effecting the operating performance of the unit. This may be accomplished by, e.g. sealing joints in apparatus 100, with, e.g. O-rings or polymers.

A portion of the Raman spectroscopy system may be, e.g. mounted outside a vehicle or an enclosure. That portion that is mounted outside the vehicle or enclosure may be, e.g. self-contained and sealed so as to resist contamination by the vehicle environment. In the event the Raman spectroscopy system becomes contaminated it may be decontaminated with the usual chemicals and cleaning procedures.

That portion that is mounted outside the vehicle or enclosure may be sealed by, e.g. incorporating "O" rings in all joints, applying a layer of a blown tar or a soft polymer to the external surfaces of the joints, or taping threaded joints with PTFE tape.

If a portion of the Raman spectroscopy system is mounted outside the vehicle or enclosure, individual components of the Raman spectroscopy system may be divided between the interior and the exterior of the vehicle. In one alternative, the laser 11, receiver telescope 24 and spectrograph 33, e.g. may be placed inside the vehicle or enclosure, with reflectors outside the vehicle or enclosure to guide the outgoing beam and the incoming elastically scattered radiation to or from them. In another alternative, the laser could also be placed outside the vehicle or enclosure. In a third alternative, the spectrograph 33 could also be placed outside the vehicle or enclosure. Other alternatives would be apparent to those skilled in the art.

Signals to be sent from the components of the Raman spectroscopy system placed outside the vehicle or enclosure may be, e.g. transmitted electrically or optically to those inside the vehicle to decouple a chemical or biological transmission path.

Signals could be, e.g. converted from electrical to optical, or vice versa, to facilitate their transmission among the various components of the system. Filters or reflectors that have to be placed in the beam path in any case may, e.g. double as ports between the inside and the outside of the vehicle. Waste heat from the laser and other components internal to the Raman spectroscopy system may be exhausted directly to the exterior without compromising decontamination compatibility.

In one embodiment, apparatus 100 includes a structure 40 made of, e.g. an aluminum honeycomb covered by carbon epoxy. Other strong, lightweight materials would be known to those skilled in the art. In a further embodiment, laser 10, beam-focusing telescope 14, receiver telescope 24, first reflector 15, second reflector 17, primary reflector 25, secondary reflector 26 spectrograph 33, and/or range-finder 29 may be mounted on structure 40. In a preferred embodiment, laser 10, beam-focusing telescope 14, receiver telescope 24, first reflector 15, second reflector 17, primary reflector 25, secondary reflector 26, spectrograph 33, and/or range-finder 29 may be mounted on structure 40 using fasteners 41, such as, e.g. a screw, a bolt, a rivet, or a pin.

In one embodiment, structure 40, laser 10, beam-focusing telescope 14, receiver telescope 24, first reflector 15, second reflector 17, primary reflector 25, secondary reflector 26, and/or range-finder 29 may be made of materials having substantially similar coefficients of thermal expansion, such as a predetermined coefficient of thermal expansion. In a preferred embodiment, predetermined coefficient of thermal expansion is a relatively low coefficient of thermal expansion, such as $1.00 \times 10^{-5}$.

In another embodiment, shown in FIG. 1, filters 30 or light baffles 31, or both, may be placed between the target substance 19 and the receiver reflector 25 to attenuate radiation at wavelength 13 from among scattered radiation 20, thus blocking elastically scattered radiation 21. Filters 30 or light baffles 31 may also be placed at other points in and around the path of inelastically scattered radiation 22, such as, e.g. along focal direction 39 to the same effect, as would be known to persons skilled in the art. For example, these elements may be placed at the output of the telescope located near the hole in the primary mirror 25. In one embodiment, filter 30 is integral with receiver telescope 24. In a preferred embodiment, filter 30 is integral with primary reflector 25.

Filter 30 may be, for example, a line or a bandstop filter whose stop band coincides with wavelength 13, or a long-pass edge filter whose pass band may be tuned to wavelengths longer than wavelength 13. Filter 30 may also be composed of a succession of short- and long-pass edge filters and reflectors that amount to a line filter or a bandstop filter, as would be known to persons skilled in the art. In this way at least some of elastically scattered radiation 21 is not processed further.

Inelastically scattered radiation 22 may be coupled from secondary reflector 26 to spectrograph 33. In one embodiment, inelastically scattered radiation 22 may be coupled from secondary reflector 26 to spectrograph 33 using an optical fiber coupling 32 having a first end 44 and a second end 45. In the alternative, optical fiber coupling 32 may be, e.g. several optical fibers, such as a bundle of optical fibers.

Spectrograph 33 includes a focal plane array (FPA) detector 34 that may be, for example, a charge coupled device (CCD). In an alternative embodiment, focal plane array detector 34 may be an intensified charge coupled device (iCCD). Spectrograph 33 further includes a diffractor 35 that may be, for example, a diffraction grating, such as a Bragg grating, or a prism, for distributing the spectrum of constituent wavelengths of inelastically scattered radiation 22 across a plane of focal plane array detector 34. The constituent wavelengths are then converted into a computer-readable signal by the focal plane array detector 34.

Figure 2:
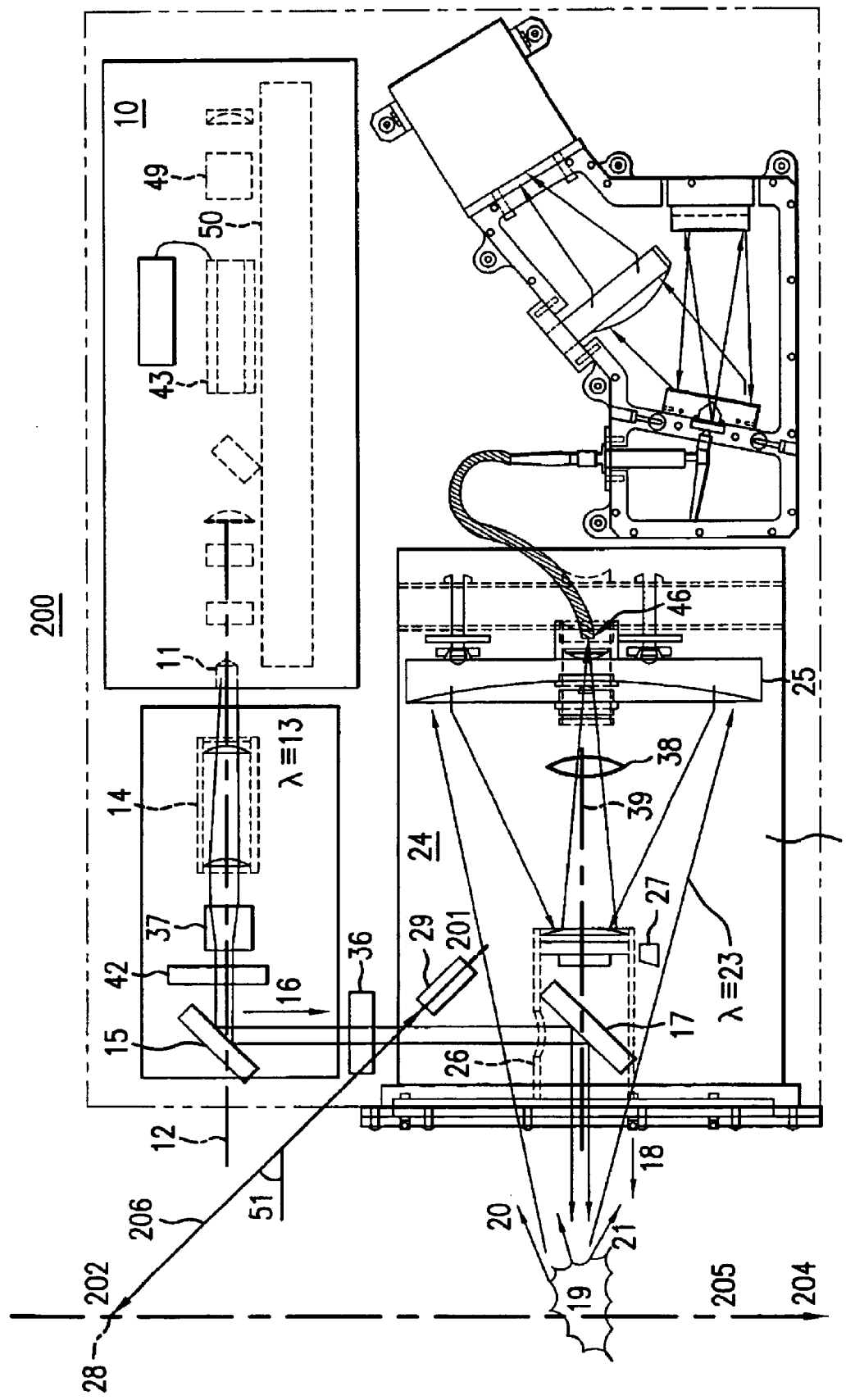
FIG. 2 is a block diagram of a range-finder according to a second embodiment of the invention.
Figure 3:
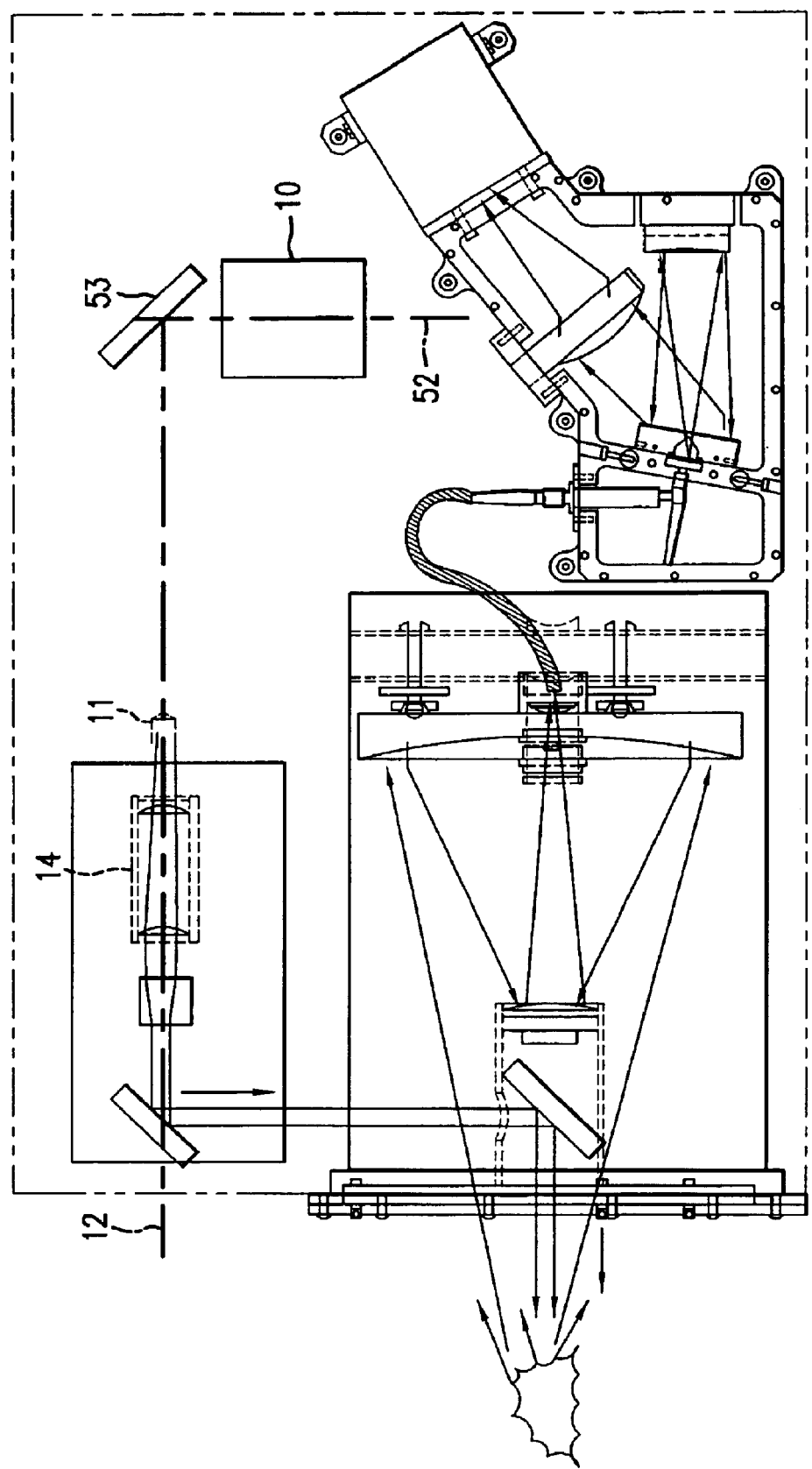
FIG. 3 is a block diagram of an alternative embodiment of the embodiment shown in FIG. 2.

In an alternative embodiment, shown in FIG. 2, reflector-focusing mechanism 27, i.e. an auto-focus, focuses secondary reflector 26 using a distance-to-target 28 signal from range-finder 29, which may be, e.g. a laser range-finder, along with a rate of relative motion 204. Secondary reflector 26 may be focused by, e.g. adjusting a position of secondary reflector 26 with an actuator such as, e.g. a voice coil actuator, an electric motor, a piezoelectric actuator, a linear motor, a pneumatic actuator, or a hydraulic actuator.

In one embodiment, rate of relative motion 204 may default to a predetermined constant. This would be the case if, e.g. rate of relative motion 204 were unavailable.

Distance-to-target 28, as the name implies, is a distance from a known point 201 within the apparatus 200, such as, e.g. the point shown in FIG. 2, to some point 202 from which the range to target substance 19 may be estimated. Such a known point 201 is preferably stationary relative to receiver reflector 25 and could be, for example, at the output of range-finder 29.

A velocity 203 of the target substance 19 relative to the apparatus 200 comprises a rate of relative motion 204 in a direction 205. Range-finder 29 outputs distance-to-target 28 signal in a third direction 206. Third direction 206 is at a forward look angle, e.g. a pre-determined non-zero angle 51, to second direction 18 in direction 205 of relative motion 204.

In one embodiment, range-finder 29 may look ahead of the target 19 as target 19 moves relative to the apparatus 200. A signal output by range-finder 29 would thus be available to predict or estimate the distance to target 19 before target 19 is at the sensing location. Telescope focus may thus be maintained, given the limiting rate of relative motion or response time of the secondary reflector 26, for any target 19 rate of relative motion and terrain condition, within the telescope's mechanical range limits.

Telescope focus may be maintained by measuring distance-to-target 28 away from target 19, in the direction of relative motion 204. In this way a focusing mechanism 27 of secondary reflector 26 may be given sufficient time to respond to a change of distance-to-target 28 and achieve proper focus for the next laser pulse. The distance ahead for which distance-to-target 28 is measured is a function of the reaction time of the focusing mechanism 27 of secondary reflector 26, focus range increment, absolute range, rate of relative motion 204, and rate of change of relative motion.

Pre-determined non-zero angle 51, i.e. the forward look angle FLA, may be a function of several variables, such as, e.g. a relative velocity of a target. Forward look angle FLA may be, e.g. adaptive, or fixed. If forward look angle FLA is fixed, on the other hand, an algorithm may be used to process e.g. the target relative velocity data to allow the angle to be adjusted for analysis conditions. Since making forward look angle FLA variable would entail an increase in mechanical complexity, a fixed forward look angle FLA is a preferred approach.

Figure 4:
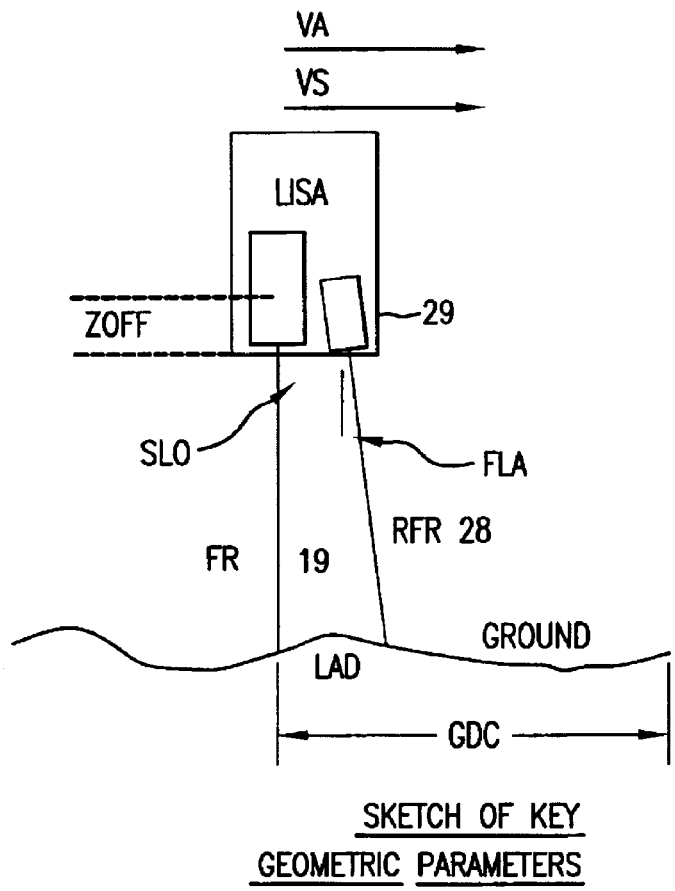
FIG. 4 shows some geometric parameters.
Figure 5:
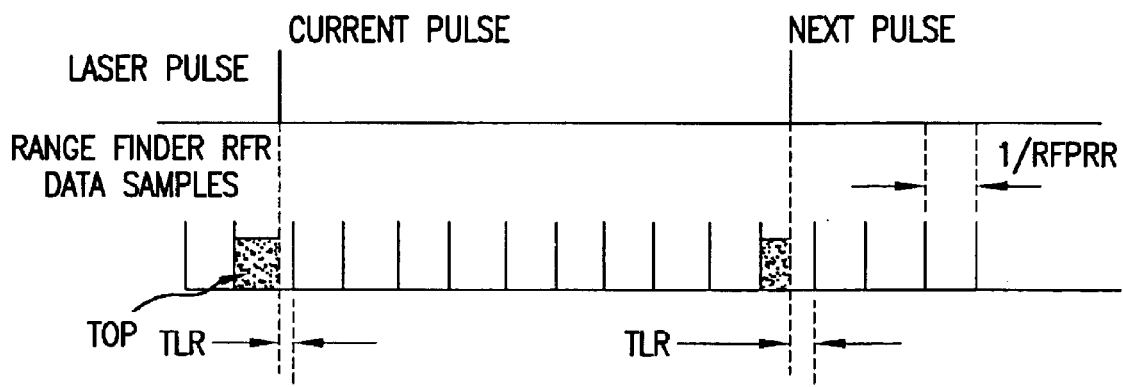
FIG. 5 shows a time interval.
Figure 6:
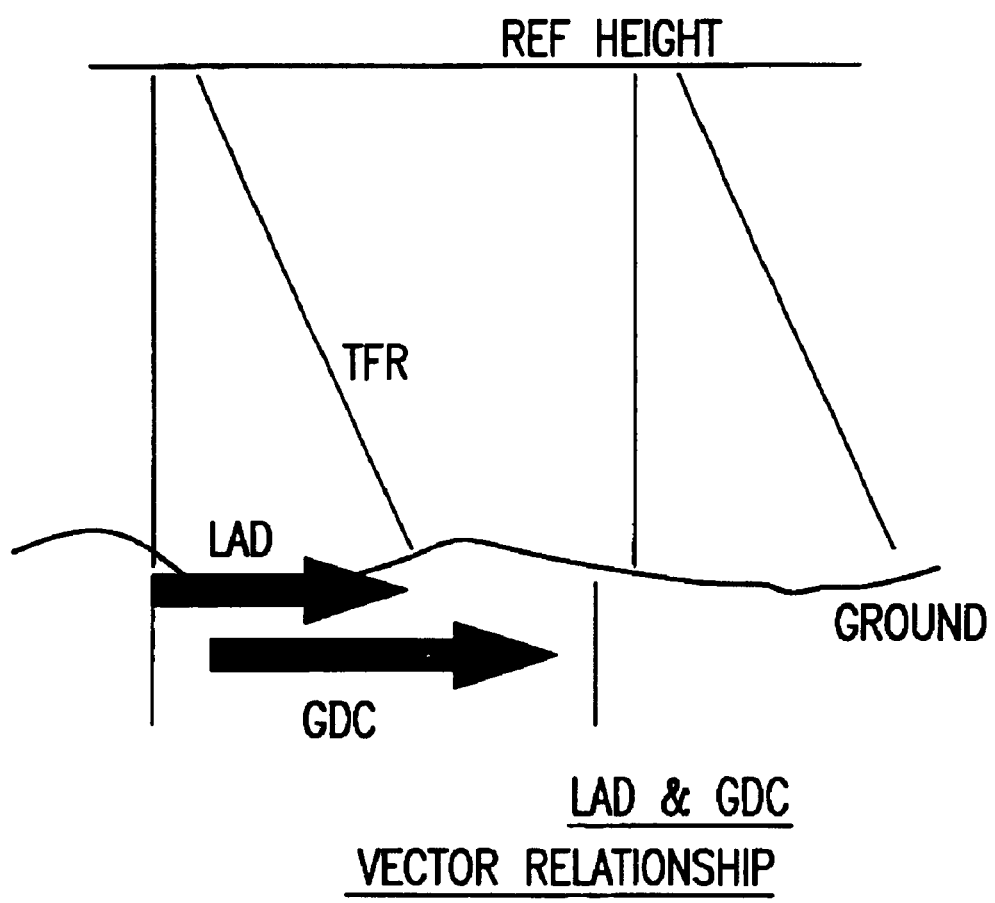
FIG. 6 shows some vectors.

Secondary reflector 26 may be adjusted by, e.g. measuring the look-ahead (slant) range at a relatively high repetition rate with range finder 29, selecting a particular range finder data sample (RFRN), and converting it to an estimate of distance-to-target 28. Distance-to-target 28 may then be used to adjust a focus of secondary reflector 26. Secondary reflector 26 may be focused based on several parameters. These factors, as shown in FIGS. 4, 5, and 6, may include, e.g. forward look angle FLA which may be a predetermined non-zero angle of the range-finder direction to the direction in which the target is viewed, ground distance covered between laser shots GDC, look ahead distance between laser & range finder spot LAD, range finder pulse rep rate in Hz RFPRR, range finder range RFR, site-line offset of range finder aperture from FR vector SLO, vehicle acceleration VA, vehicle speed VS, time between laser pulse and range finder RFR sample data TLR.

A particular range finder 29 data sample that represents, e.g. the range to the next target 19 is referred to as the range finder number RFRN. Range finder number RFRN may be identified with the following equation:

$$RFRN = ROUND[((GDC-LAD)/RFGD)+SOC] \quad \text{(eq 41-1)}$$

Where;

$$LAD = SLO + RFR * SIN\ FLA \quad \text{(eq 41-2)}$$

$$GDC = VS * TLP + 0.5 * VA * TLP2 \quad \text{(eq 41-3)}$$

$$RFGD = VS * TRP + 0.5 * VA * TRP2 \quad \text{(eq 41-4)}$$

$$VA = (VSn - VSn-k)/k * TLP \quad \text{(eq 41-5)}$$

where K=1, 2, 3 . . . , the sample interval $$SOC = RFSD + (1 - (TLR * RFPRR))$$

The terms of equations 41-1 through 41-5 may be defined as follows:
FLA Forward Look Angle of Range Finder
GDC Ground Distance Covered Between Laser Shots
LAD Look Ahead Distance Between Laser & Range Finder Spot
RFPRR Range Finder Pulse Rep Rate-Hz
RFGD Range Finder Ground distance
RFR Range Finder Range
RFSD Range Finder Sample Delay
RFRN Range Finder Number (RFR selection)
SLO Site-line offset of range finder aperture from FR vector—measured parallel to VS vector
Soc Sample Offset Correction (adjusts calculated RFR sample tag number for time offset between laser pulse and range finder pulse)
TLP Time to next Laser Pulse-ms
Time between Laser pulse and Range finder RFR sample data
TRP Time between Range finder Pulses
VA Vehicle Acceleration
VS Vehicle Speed RFRN may be selected based on several subsystem parameters and results in a correct telescope focus in the presence of varying external system parameters of vehicle acceleration and velocity and changing ground slope.

In one embodiment, shown in FIG. 1, optical fiber 32 may be a circular-to-line optical fiber bundle whose output geometry matches the geometry of focal plane array detector 34, for maximal coupling with highest spectral resolution of inelastically scattered radiation 22 to focal plane array detector 34. Additional coupling optics may be required to efficiently couple the light from secondary reflector 26 to optical fiber 32. These optics may also include the optical filter to remove elastically scattered radiation at wavelength 13.

In another embodiment, first end 44 of optical fiber 32 may be substantially coincident with first focal point 46. First end 44 may be, e.g. a convex surface to allow secondary reflector 26 to have some range of motion while still coupling inelastically scattered radiation 22 efficiently. Second end 45 may be centered in diffractor 35. In a further embodiment, second end 45 may be integral to diffractor 35.

Spectrograph 33 may further include a parabolic reflector 47 to receive inelastically scattered radiation 22 dispersed from second end 45. Second end 45 may be coincident with a focal point 48 of parabolic reflector 47. Parabolic reflector 47 will thus collimate dispersed inelastically scattered radiation 22 towards diffractor 35.

In an alternate embodiment, the spectrograph 33 may be located at a distance from the sensor, possibly housed with an analysis computer internal to the vehicle. In this case, an additional optical fiber may be used to couple the light from the optics at the rear of the telescope to the spectrograph. In an alternative embodiment, the spectrograph and related equipment may be coupled to the receiver telescope with, e.g. an infrared, electronic, or inductive link, in order to decouple a chemical or biological contamination path into the vehicle.

Finally, the signal from focal plane array detector 34 may be coupled to appropriate software for comparing the detected spectral array to a library of spectral arrays of known chemical agents until a match is found, or the signal is determined to be an unknown or new chemical agent. If, e.g. the signal is undetermined, it may be added to the database so that statistics can be collected for further analysis.

Figure 7:
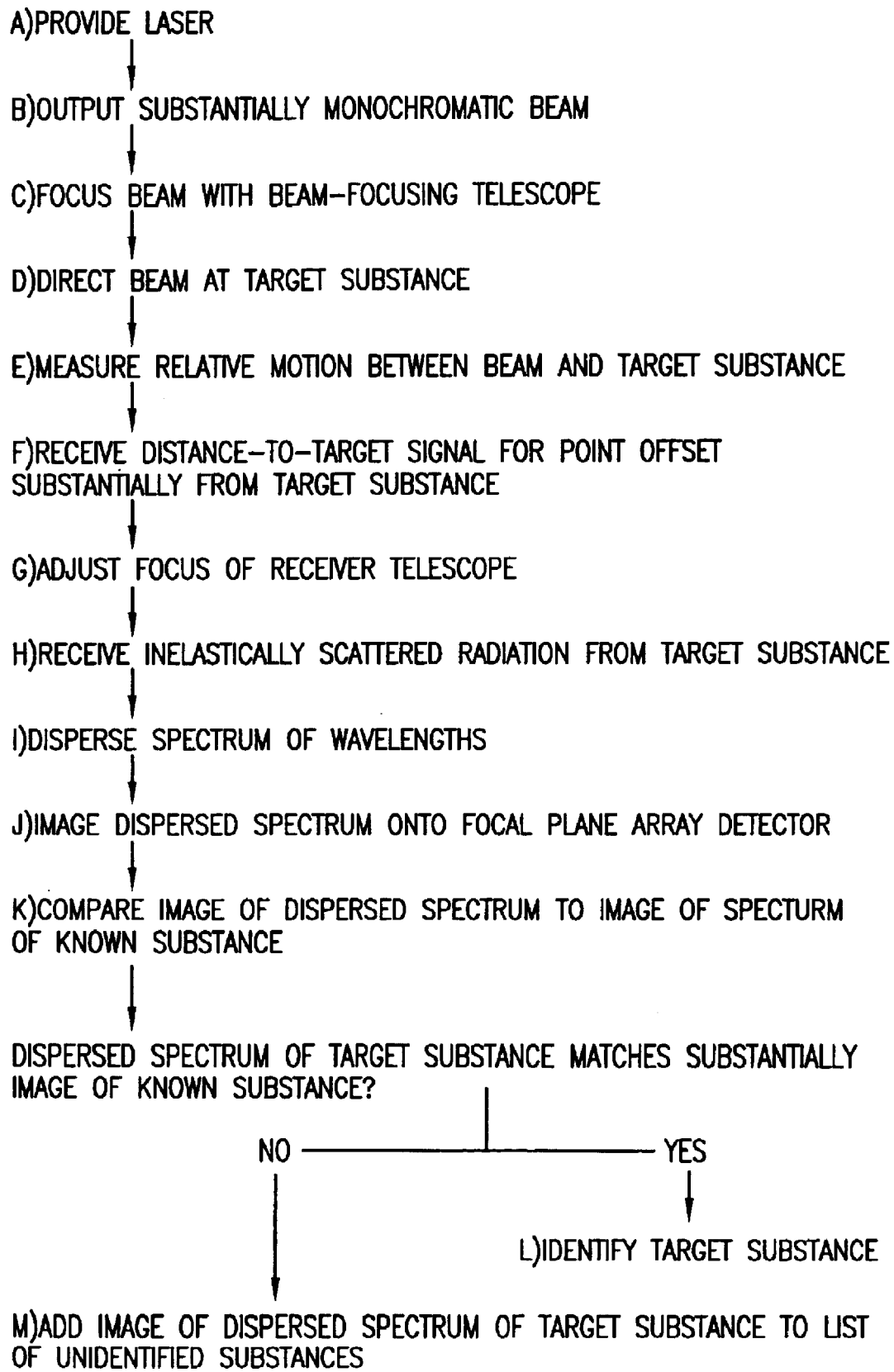
FIG. 7 shows a method according to a fourth embodiment of the invention.

In a fourth embodiment, as shown in FIG. 7, the invention comprises a method for laser interrogation of surface agents moving relative to an interrogator including the steps of providing a laser, outputting a substantially monochromatic beam from the laser, focusing the beam with a beam-focusing telescope, directing the beam at a target substance, measuring a relative motion between beam and target substance, receiving a distance-to-target signal for a point offset substantially from target substance, adjusting a focus of a receiver telescope based on relative motion and distance-to-target signal, receiving inelastically scattered radiation from the target substance at a spectrum of wavelengths characteristic of the target substance with the receiver telescope, dispersing the spectrum of wavelengths of the inelastically scattered radiation, imaging the dispersed spectrum onto a focal plane array detector, comparing the image of the dispersed spectrum of the target substance to an image of a spectrum of inelastically scattered radiation of a known substance, identifying the target substance if the image of the dispersed spectrum of the target substance matches substantially the image of the inelastically scattered radiation of the known substance, and adding the target substance to a list of unidentified substances if the image of the dispersed spectrum of the target substance does not substantially match any image in database.

Figure 8:
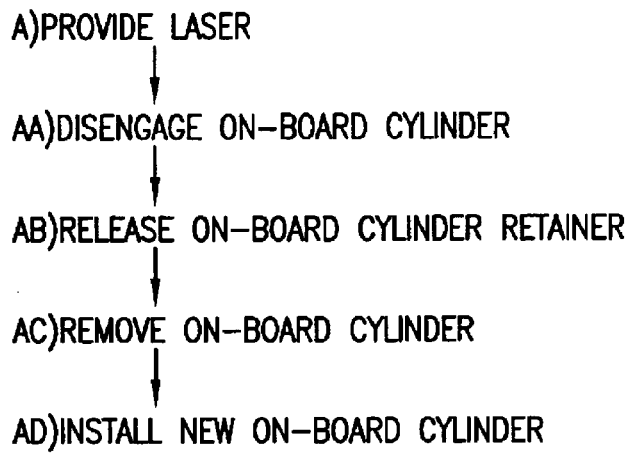
FIG. 8 shows a second embodiment of the method shown in FIG. 7.
Figure 9:
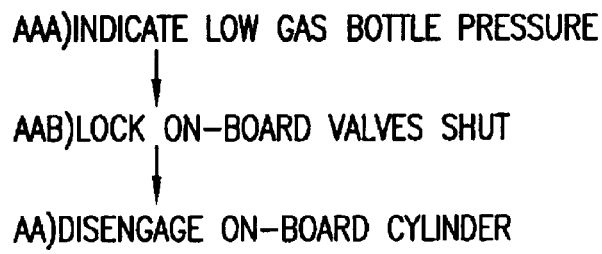
FIG. 9 shows a third embodiment of the method shown in FIG. 7.
Figure 10:
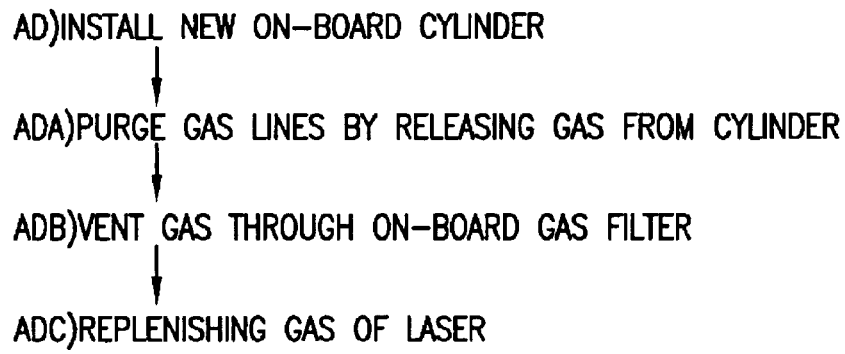
FIG. 10 shows a fourth embodiment of the method shown in FIG. 7.
Figure 11:
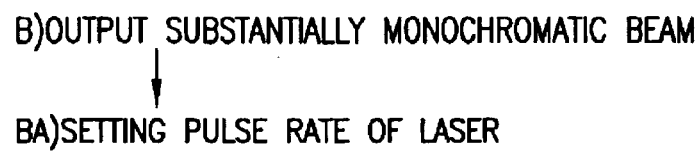
FIG. 11 shows a fifth embodiment of the method shown in FIG. 7.

As shown in FIG. 8, the step of providing a laser in the method for laser interrogation of surface agents may comprise further the steps of disengaging an on-board cylinder, releasing an on-board cylinder retainer, removing on-board cylinder, and installing a new on-board cylinder. As shown in FIG. 9, the step of disengaging an on-board cylinder may be preceded by the steps of indicating a low gas bottle pressure and locking on-board valves shut. As shown in FIG. 10, the step of installing a new on-board cylinder may be followed by the steps of purging gas lines by releasing gas from on-board cylinder, venting gas through on-board cylinder gas filter, and replenishing a gas in a laser. As shown in FIG. 11, the step of outputting a substantially monochromatic beam from the laser in the method for laser interrogation of surface agents further includes setting a pulse rate of the laser.

As shown in FIG. 12, the step of adjusting a focus of a receiver telescope may comprise further the steps of receiving a range-to-target data sample, tagging the range-to-target data sample with a time sequence, receiving a relative motion data sample, calculating a rate of change of the relative motion, correcting the range-to-target data sample for the relative motion, correcting the range-to-target data sample for rate of change of the relative motion, correcting the range-to-target data sample for a laser pulse rate, correcting the range-to-target data sample for a range-finder pulse rate, correcting the range-to-target data sample for range-finder position relative to a receiver telescope line-of-sight, correcting the tagged range-to-target data sample for a waveform de-synchronization time offset, transforming a set of co-ordinates of corrected tagged range-finder sample to a receiver telescope line-of-sight, and converting range-to-target sample to an equivalent receiver telescope secondary reflector position.

In an alternative embodiment the step of identifying the target substance in the method for laser interrogation of surface agents is carried out in substantially real time.

While the invention has been described in detail above, the invention is not intended to be limited to the specific embodiments as described. It is evident that those skilled in the art may now make numerous uses and modifications of and departures from the specific embodiments described herein without departing from the inventive concepts.

What is claimed is:

1. An apparatus for laser interrogation of surface agents moving relative to the apparatus, said apparatus comprising:
    a laser, said laser outputting an output beam;
    a beam-focusing telescope having an axis of transmission, said beam-focusing telescope receiving and focusing substantially said output beam;
    a first reflector substantially aligned with said axis of transmission for directing said output beam in a first direction, said first direction being substantially perpendicular to the axis of transmission;
    a second reflector substantially aligned with said first direction for directing said output beam in a second direction, said second direction being substantially perpendicular to said first direction;
    a receiver telescope, said receiver telescope having a focal direction substantially opposite to said second direction, said receiver telescope comprising further:
    a primary reflector, said primary reflector disposed to reflect at least some radiation scattered inelastically from a target;
    a focusable secondary reflector disposed to reflect and focus said inelastically scattered radiation toward a first focal point;
    a secondary reflector focusing mechanism to move said focusable secondary reflector along said focal direction;
    a spectrograph, said spectrograph receiving said inelastically scattered radiation from said receiver telescope;
    a range-finder, said range-finder outputting a distance-to-target signal in a third direction;
    wherein said third direction is at a predetermined non-zero angle to said second direction in a direction of said relative motion; and
    wherein said focusing mechanism moves said secondary reflector based on said distance-to-target signal and a rate of said relative motion to focus substantially said inelastically scattered radiation at said first focal point.

2. The apparatus of claim 1, wherein said range-finder is a laser range-finder.

3. The apparatus of claim 1, wherein said first reflector transmits substantially visible light.

4. The apparatus of claim 1, wherein said second reflector transmits substantially visible light.

5. The apparatus of claim 1, wherein said primary reflector transmits substantially visible light.

6. The apparatus of claim 1, wherein said secondary reflector transmits substantially visible light.

7. The apparatus of claim 1, wherein said focusing mechanism comprises an actuator selected from the group consisting of:
    a voice coil actuator,
    an electric motor,
    a piezoelectric actuator,
    a linear motor,
    a pneumatic actuator, and
    a hydraulic actuator.

8. The apparatus of claim 1, wherein said rate of said relative motion defaults to a predetermined constant.

9. The apparatus of claim 1, wherein:
    a portion of said output beam is at a predetermined wavelength, and said predetermined wavelength is less than approximately 253 nm.

10. The apparatus of claim 9, wherein:
    said predetermined wavelength is 248 nm.

11. The apparatus of claim 9, wherein said primary reflector transmits substantially radiation at said predetermined wavelength.

12. The apparatus of claim 9, wherein said secondary reflector transmits substantially radiation at said predetermined wavelength.

13. The apparatus of claim 1, wherein a portion of said output beam is of a predetermined polarization.

14. The apparatus of claim 13, wherein said output beam comprises further amplified spontaneous emission (ASE), said ASE being substantially unpolarized;
    said apparatus comprising further a polarized reflector aligned substantially with said axis of transmission, said polarized reflector transmitting said ASE.

15. The apparatus of claim 13, wherein said output beam comprises further amplified spontaneous emission (ASE), said ASE being substantially unpolarized;
    said apparatus comprising further a polarized reflector aligned substantially with said axis of transmission, said polarized reflector reflecting said ASE.

16. The apparatus of claim 1, comprising further an aluminum honeycomb structure; and
    wherein said laser, said beam-focusing telescope, said first reflector, said second reflector, said range finder, and said receiver telescope are fixedly disposed on said structure.

17. The apparatus of claim 16, wherein said structure comprises a predetermined coefficient of thermal expansion.

18. The apparatus of claim 16, wherein said laser, said beam-focusing telescope, said first reflector, said second reflector, said receiver telescope, said primary reflector, said focusable secondary reflector, and said range-finder further comprise a predetermined coefficient of thermal expansion.

19. The apparatus of claim 16, wherein said aluminum honeycomb structure comprises further a carbon epoxy covering.

20. The apparatus of claim 16, wherein one of said laser, said beam-focusing telescope, said first reflector, said second reflector, said range finder, and said receiver telescope are fixedly disposed on said structure with a fastener, said fastener selected from the group consisting of:
   a screw,
   a bolt,
   a rivet, and
   a pin.

21. The apparatus of claim 1, wherein said laser emits pulses at a pulse rate, and said pulse rate is selected from the group consisting of:
   a predetermined pulse rate,
   a variable pulse rate,
   an operator-controlled pulse rate, and
   a pulse rate proportional to a rate of said relative motion.

22. The apparatus of claim 1, further comprising:
   a receiver telescope filter coincident with said focal direction, said filter being substantially opaque to elastically scattered radiation.

23. The apparatus of claim 22, wherein said receiver telescope filter is integral with said receiver telescope.

24. The apparatus of claim 23, wherein said receiver telescope filter is integral with said primary reflector.

25. The apparatus of claim 22, wherein said receiver telescope filter is an edge filter.

26. The apparatus of claim 1, wherein said laser is an Alexandrite laser.

27. The apparatus of claim 26, wherein said laser is a line-narrowed Alexandrite laser.

28. The apparatus of claim 1, wherein said laser is an Excimer laser.

29. The apparatus of claim 28, wherein said laser is a line-narrowed Excimer laser.

30. The apparatus of claim 28, wherein said laser comprises further a replaceable gas bottle.

31. The apparatus of claim 1, wherein said apparatus is substantially resistant to a decontamination chemical.

32. The apparatus of claim 1, comprising further:
   an optical fiber coupling said inelastically scattered radiation from said receiver telescope to said spectrograph.

33. The apparatus of claim 32, wherein said optical fiber comprises a bundle of optical fibers.

34. The apparatus of claim 32, wherein said optical fiber comprises further a first end and a second end;
   said first end being substantially coincident with said first focal point to collect said inelastically scattered radiation;
   said spectrograph comprising further:
   a parabolic reflector, said second end being substantially coincident with a focal point of said parabolic reflector to disperse said inelastically scattered radiation;
   said parabolic reflector disposed to reflect said dispersed inelastically scattered radiation toward a diffraction grating, said diffraction grating diffracting said dispersed inelastically scattered radiation; and
   a focal plane array detector receiving said diffracted inelastically scattered radiation.

35. The apparatus of claim 34, wherein:
   said focal plane array detector has a first predetermined geometry;
   said optical fiber comprises a circular-to-line optical fiber having a second predetermined geometry; and
   said second predetermined geometry matches said first predetermined geometry.

36. The apparatus of claim 34, wherein said focal plane array detector is selected from a group consisting of:
   an intensified charge coupled device, and
   a charge coupled device.

37. The apparatus of claim 34, wherein said second end is centered in said diffraction grating.

38. The apparatus of claim 34, wherein said second end is integral to said diffraction grating.

39. The apparatus of claim 1, wherein said output beam comprises wavelengths other than said predetermined wavelength, said apparatus comprising further:
   an output filter adapted to attenuate said wavelengths other than said predetermined wavelength.

40. The apparatus of claim 1, wherein said laser comprises further a lens, said lens fixedly disposed in said laser with at least one retaining ring.

41. The apparatus of claim 1, wherein said beam-focusing telescope comprises further a lens, said lens fixedly disposed in said beam-focusing telescope with at least one retaining ring.

42. The apparatus of claim 1, wherein said laser has an output axis, said apparatus comprising further:
   a third reflector aligned substantially with said output axis, said third reflector redirecting said output beam along said axis of transmission.

43. A method for laser interrogation of surface agents moving relative to an interrogator, said method comprising the steps of:
   a) providing a laser;
   b) outputting a substantially monochromatic beam from said laser;
   c) focusing said beam with a beam-focusing telescope;
   d) directing said beam at a target substance;
   e) measuring a relative motion between said beam and said target substance;
   f) receiving a distance-to-target signal for a point offset substantially from said target substance;
   g) adjusting a focus of a receiver telescope based on said relative motion and said distance-to-target signal;
   h) receiving inelastically scattered radiation from said target substance at a spectrum of wavelengths characteristic of said target substance with said receiver telescope;
   i) dispersing said spectrum of wavelengths of said inelastically scattered radiation;
   j) imaging said dispersed spectrum onto a focal plane array detector;
   k) comparing said image of said dispersed spectrum of said target substance to an image of a spectrum of inelastically scattered radiation of a known substance; and
   l) identifying said target substance if said image of said dispersed spectrum of said target substance matches substantially said image of said inelastically scattered radiation of said known substance.

44. The method of claim 43, comprising further:
m) adding said image of said dispersed spectrum of said target substance to a list of unidentified substances if said image of said dispersed spectrum of said target substance does not substantially match an image of a spectrum of inelastically scattered radiation of a known substance.

45. The method of claim 43, said step of providing a laser comprising further:
aa) disengaging an on-board cylinder,
ab) releasing an on-board cylinder retainer;
ac) removing said on-board cylinder; and
ad) installing a new on-board cylinder.

46. The method of claim 45, said step of disengaging an on-board cylinder comprising further:
aaa) indicating a low gas bottle pressure; and
aab) locking on-board valves shut.

47. The method of claim 45, said step of installing a new on-board cylinder comprising further:
ada) purging gas lines by releasing gas from cylinder;
adb) venting gas through on-board gas filter; and
adc) replenishing a gas of said laser.

48. The method of claim 43, wherein said step of outputting a substantially monochromatic beam from said laser further comprises setting a pulse rate of said laser.

49. The method of claim 43, wherein said step of adjusting a focus of a receiver telescope comprises further:
ga) receiving a range-to-target data sample;
gb) tagging said range-to-target data sample with a time sequence;
gc) receiving a relative motion data sample;
gd) calculating a rate of change of said relative motion;
ge) correcting said range-to-target data sample for said relative motion;
gf) correcting said range-to-target data sample for rate of change of said relative motion;
gg) correcting said range-to-target data sample for a laser pulse rate;
gh) correcting said range-to-target data sample for a range-finder pulse rate;
gi) correcting said range-to-target data sample for range-finder position relative to a receiver telescope line-of-sight;
gj) correcting said tagged range-to-target data sample for a laser and range-finder waveform de-synchronization time offset;
gk) transforming a set of co-ordinates of corrected tagged range-finder sample to a receiver telescope line-of-sight; and
gl) converting said range-to-target sample to an equivalent receiver telescope secondary reflector position.

50. The method of claim 43, wherein said step of identifying said target substance is carried out substantially in real time.

51. A system for laser interrogation of surface agents moving relative to the system, said system comprising:
a laser, said laser outputting an output beam;
a beam-focusing telescope having an axis of transmission, said beam-focusing telescope receiving and focusing substantially said output beam;
a first reflector substantially aligned with said axis of transmission for directing said output beam in a first direction, said first direction being substantially perpendicular to the axis of transmission;
a second reflector substantially aligned with said first direction for directing said output beam in a second direction, said second direction being substantially perpendicular to said first direction;
a receiver telescope, said receiver telescope having a focal direction substantially opposite to said second direction, said receiver telescope comprising further:
a primary reflector, said primary reflector disposed to reflect at least some radiation scattered inelastically from a target;
a focusable secondary reflector disposed to reflect and focus said inelastically scattered radiation toward a first focal point;
a secondary reflector focusing mechanism to move said focusable secondary reflector along said focal direction;
a spectrograph, said spectrograph receiving said inelastically scattered radiation from said receiver telescope;
means for range finding, said range finding means outputting a distance-to-target signal in a third direction;
wherein said third direction is at a predetermined angle to said second direction in a direction of said relative motion; and
wherein said focusing mechanism moves said secondary reflector based on said distance-to-target signal and a rate of said relative motion to focus substantially said inelastically scattered radiation at said first focal point.

52. An apparatus for laser interrogation of surface agents moving relative to the apparatus, said apparatus comprising:
an aluminum honeycomb structure;
a laser fixedly disposed on said structure, said laser outputting an output beam;
a beam-focusing telescope fixedly disposed on said structure and having an axis of transmission, said beam-focusing telescope receiving and focusing substantially said output beam;
a first reflector fixedly disposed on said structure and substantially aligned with said axis of transmission for directing said output beam in a first direction, said first direction being substantially perpendicular to the axis of transmission;
a second reflector fixedly disposed on said structure and substantially aligned with said first direction for directing said output beam in a second direction, said second direction being substantially perpendicular to said first direction;
a receiver telescope, said receiver telescope having a focal direction substantially opposite to said second direction, said receiver telescope comprising further:
a primary reflector, said primary reflector disposed to reflect at least some radiation scattered inelastically from a target;
a focusable secondary reflector disposed to reflect and focus said inelastically scattered radiation toward a first focal point;
a secondary reflector focusing mechanism to move said focusable secondary reflector along said focal direction;
a spectrograph fixedly disposed on said structure, said spectrograph receiving said inelastically scattered radiation from said receiver telescope;
a range-finder fixedly disposed on said structure and outputting a distance-to target signal;

wherein said focusing mechanism focuses said secondary reflector based on said distance-to-target signal.

53. The apparatus of claim 52, wherein said structure comprises a predetermined coefficient of thermal expansion.

54. The apparatus of claim 52, wherein said laser, said beam-focusing telescope, said first reflector, said second reflector, said receiver telescope, said primary reflector, said focusable secondary reflector, and said range-finder further comprise a predetermined coefficient of thermal expansion.

55. The apparatus of claim 52, wherein said aluminum honeycomb structure comprises further a carbon epoxy covering.

56. The apparatus of claim 52, wherein each of said laser, said beam-focusing telescope, said first reflector, said second reflector, and said receiver telescope are fixedly disposed on said structure with a fastener, said fastener selected from the group consisting of:

a screw, a bolt, a rivet, and a pin.

57. An apparatus for laser interrogation of surface agents moving relative to the apparatus, said apparatus comprising:

a laser, said laser outputting an output beam;

a beam-focusing telescope having an axis of transmission, said beam-focusing telescope receiving and focusing substantially said output beam;

a first reflector substantially aligned with said axis of transmission for directing said output beam in a first direction, said first direction being substantially perpendicular to the axis of transmission;

a second reflector substantially aligned with said first direction for directing said output beam in a second direction, said second direction being substantially perpendicular to said first direction;

a receiver telescope, said receiver telescope having a focal direction substantially opposite to said second direction, said receiver telescope comprising further:

a primary reflector, said primary reflector disposed to reflect at least some radiation scattered inelastically from a target;

a focusable secondary reflector disposed to reflect and focus said inelastically scattered radiation toward a first focal point;

a secondary reflector focusing mechanism to move said focusable secondary reflector along said focal direction;

an optical fiber having a first end and a second end coupling said inelastically scattered radiation from said receiver telescope to a spectrograph;

said first end being substantially coincident with said first focal point to collect said inelastically scattered radiation;

said spectrograph comprising further:

a parabolic reflector, said second end being substantially coincident with a focal point of said parabolic reflector to disperse said inelastically scattered radiation;

said parabolic reflector disposed to reflect said dispersed inelastically scattered radiation toward a diffraction grating said second end being integral to said diffraction grating, said diffraction grating diffracting said dispersed inelastically scattered radiation; and a focal plane array detector receiving said diffracted inelastically scattered radiation;

a range-finder outputting a distance-to-target signal;

wherein said focusing mechanism focuses said secondary reflector based on said distance-to-target signal.

58. The apparatus of claim 57, wherein said optical fiber comprises a bundle of optical fibers.

59. The apparatus of claim 57, wherein:

said focal plane array detector has a first predetermined geometry;

said optical fiber comprises a circular-to-line optical fiber having a second predetermined geometry; and said second predetermined geometry matches said first predetermined geometry.

60. An apparatus for laser interrogation of a target moving in a direction of motion relative to the apparatus, the apparatus comprising:

a laser that supplies a beam that strikes the target upon the target entering a predetermined sensing location;

a focusable receiver that receives a portion of radiation scattered inelastically from the target in response to the laser beam striking the target and focuses the inelastically scattered radiation at a focal point;

a spectrograph that receives the focused inelastically scattered radiation from the focusable receiver; and a range-finder that determines a distance-to-target in response to the target entering a location that is a predetermined distance from the sensing location in the direction of relative motion;

wherein the focusable receiver is focused based on the determined distance-to-target signal and a rate of the relative motion to focus the received inelastically scattered radiation at the focal point.

61. The apparatus of claim 60, further comprising an optical fiber coupling the focusable receiver to the spectrograph.

62. The apparatus of claim 60, wherein the apparatus is mounted on a ground-based platform and analyzes ground-based targets.

63. An apparatus for laser interrogation of surface agents moving relative to the apparatus, said apparatus comprising:

a laser that generates an output beam;

a beam-focusing telescope having an axis of transmission in a first direction, the beam-focusing telescope focusing the output beam;

a reflector substantially aligned with the first direction for directing the output beam in a second direction;

a receiver telescope having a focal direction substantially opposite to the second direction, the receiver telescope comprising: a primary reflector disposed to reflect at least some radiation scattered inelastically from a target; a focusable secondary reflector disposed to reflect and focus the inelastically scattered radiation toward a first focal point; a secondary reflector focusing mechanism that moves the focusable secondary reflector along the focal direction;

a spectrograph that receives the inelastically scattered radiation from the receiver telescope;

a range-finder that generates a distance-to-target signal in a third direction;

wherein the third direction is at a predetermined non-zero angle to the second direction in a direction of the relative motion; and wherein the focusing mechanism moves the secondary reflector based on the distance-to-target signal and a rate of the relative motion to focus substantially the inelastically scattered radiation at the first focal point.

64. The apparatus of claim 63, wherein the laser emits pulses at a pulse rate, and the pulse rate is selected from the group consisting of:

a predetermined pulse rate, a variable pulse rate, an operator-controlled pulse rate, and a pulse rate proportional to a rate of relative motion of the target relative to the apparatus.

* * * * *